United States Patent [19]

Chauvette

[11] 4,316,842
[45] Feb. 23, 1982

[54] PENICILLIN INTERMEDIATES

[75] Inventor: Robert R. Chauvette, Indianapolis, Ind.

[73] Assignee: Eli Lilly and Company, Indianapolis, Ind.

[21] Appl. No.: 209,439

[22] Filed: Nov. 24, 1980

[51] Int. Cl.³ ............................................ C07D 499/02
[52] U.S. Cl. ............................. 260/245.2 R; 424/270; 424/271; 260/239 A; 260/239.1
[58] Field of Search ..................... 260/245.2 R, 239.1; 427/270; 424/271

[56] References Cited

PUBLICATIONS

Journal of Pharmaceutical Sciences, 68, No. 10, pp. 1207–1215, 1979.

F. J. Lund, "6β-Amidinopenicillanic Acids–Synthesis and Antibacterial Properties," Recent Advances in the Chemistry of β-Lactam Antibiotics, Ed. J. Elks, Specialist Publication-Chemical Society, No. 28, 1977, pp. 25–45.

Primary Examiner—Nicholas S. Rizzo
Attorney, Agent, or Firm—William B. Scanlon; Arthur R. Whale

[57] ABSTRACT

6-Epi penicillin α-sulfoxides represented by the formula

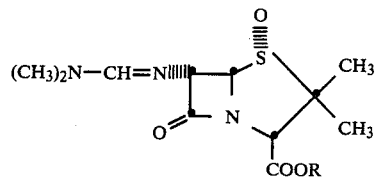

wherein R is a carboxy protecting group, are useful for preparing antibiotic compounds and are prepared via epimerization with an alkali metal acetate of corresponding 6β-epimer.

5 Claims, No Drawings

PENICILLIN INTERMEDIATES

SUMMARY OF THE INVENTION

The present invention provides 6-epiamidinopenicillin ester 1α-oxides and a process for the preparation thereof. The 6-epi penicillin sulfoxide esters are intermediates having the correct stereochemistry for use in the synthesis of certain 1-oxa-β-lactam antibiotic compounds.

The 6-epi penicillin sulfoxides are prepared by reacting an ester of 6-aminopenicillanic acid with dimethylformamide dimethylacetal to form a 6β-[(dimethylaminomethylene)amino]penicillanic acid ester and, after oxidizing the product with potassium peroxymonosulfate ($2K_2HSO_5 \cdot KHSO_4 \cdot K_2SO_4$) to form the α-sulfoxide (1α-oxide), the 6β-amidino group of the α-sulfoxide ester is epimerized with an alkali metal acetate in an aqueous medium to the 6α-amidino-α-sulfoxide ester.

The 6-epi penicillin sulfoxides provided by this invention are converted to the corresponding 6α-formamidopenicillanic acid ester α-sulfoxides with a weak carboxylic acid, a percarboxylic acid, or a phenol having a pH as measured in water of between about 2 and about 5. The 6α-formamido sulfoxide esters are useful intermediates in the process for preparing 1-oxa-β-lactam antibiotics.

DETAILED DESCRIPTION OF THE INVENTION

The 6-epi penicillin ester sulfoxides provided by this invention are represented by the following structural formula 1

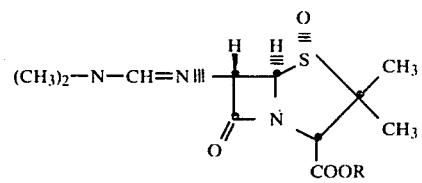

wherein R is a carboxy-protecting group, and the acid addition salt thereof.

The compounds of the formula 1 are formally named as 6α-[(dimethylaminomethylene)amino]-2,2-dimethylpenam-4-carboxylic acid ester 1α-oxides. For convenience herein, the dimethylaminomethyleneamino substituent is referred to as the dimethylamidino group.

In the above formula 1 the dotted bonding lines indicate that the dimethylamidino group and the 1-oxide (sulfoxide) have the α-configuration and thus are located behind the plane of the β-lactam ring. This configuration of the substituent in the 6-position of the penam is isomeric with the natural or β-configuration of the 6-position side chain of the penicillin antibiotics such as penicillin G and penicillin V. Accordingly, the compounds of the invention are referred to as 6-epi dimethylamidino penicillin ester 1α-oxides or as 6α-dimethylamidino penicillin ester 1α-oxides.

The compounds provided by the invention are readily prepared in excellent yields as follows.

An ester of 6-aminopenicillanic acid is converted to a 6β-dimethylamidino penicillin ester with dimethylformamide dimethylacetal, and the product is oxidized to the corresponding 6β-dimethylamidino penicillin α-sulfoxide ester. The 6β-dimethylamidino group of the α-sulfoxide is then epimerized to provide the 6α-dimethylamidino penicillin α-sulfoxide ester of the invention.

The first step in the synthesis is carried out by reacting an ester of 6-aminopenicillanic acid (6APA) with dimethylformamide dimethylacetal at room temperatures to provide the 6β-[(dimethylaminomethylene)amino]-2,2-dimethylpenam-4-carboxylic acid ester as illustrated by the following reaction scheme.

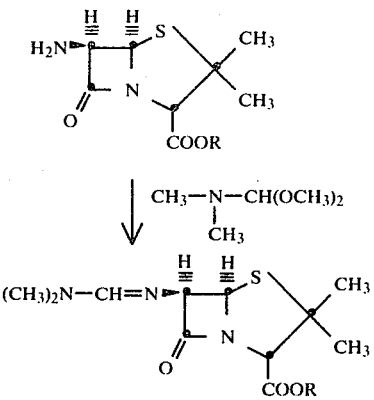

wherein R is a carboxy-protecting group.

The reaction is best carried out by using the DMF dimethylacetal in sufficient excess so that the reagent also can serve as the solvent. Alternatively, a slight molar excess of the acetal can be used when an inert organic solvent is employed. Solvents such as acetonitrile, tetrahydrofuran, DMF, or dimethylacetamide can be used.

The reaction can be carried out conveniently at or near room temperature under substantially anhydrous conditions. Under these conditions the formation of the dimethylamidino penicillin ester is essentially complete in about 2 to about 4 hours with stirring.

The dimethylamidino derivative also can be prepared by the reaction of a 6APA ester with phosphorus trichloride in dimethylformamide under Villsmeyer conditions. However, higher yields of the product are obtained with the dimethylacetal of dimethylformamide than with $PCl_3$-DMF under Villsmeyer conditions.

The 6β-dimethylamidino penicillin ester is then oxidized to form the corresponding α-sulfoxide ester. The oxidation is preferably carried out by reacting the dimethylamidino ester with potassium peroxymonosulfate in an aqueous medium containing a water miscible, non-oxidizable, organic solvent such as acetonitrile or tetrahydrofuran. The organic solvent functions to solubilize the penicillin ester in the aqueous medium containing the oxidizing agent. The oxidizing agent, potassium peroxymonosulfate ($2KHSO_5 \cdot KHSO_4 \cdot K_2SO_4$), is described by R. J. Kennedy, et al., *J. Org. Chem.* 25, 1901 (1960).

The oxidizing agent is used in excess, preferably at between about 0.1 M and about 0.2 M excess, i.e., for each mole or fraction thereof of penicillin ester used between about 1.1 and 1.2 moles of the oxidant are used.

The sulfoxide formation proceeds at a satisfactory rate when carried out at or near room temperatures. When carried out on a laboratory scale, the formation of the sulfoxide is substantially complete in an hour or less. Under the above conditions, yields of the 6β-dimethylamidino penicillin ester 1α-oxide of about 70% are generally obtained.

The α-sulfoxides (1α-oxides) are readily isolated from the reaction mixture as crystalline solids as follows. After the reaction is complete, the pH of the mixture is adjusted to about pH 6.5 with 1 N sodium hydroxide or other suitable base. The mixture is then evaporated to remove the organic solvent and, while the aqueous concentrate is slurried with a water immiscible organic solvent such as ethyl acetate, the pH is readjusted to about pH 8. The organic solvent is separated from the aqueous phase, is washed with water, dried, and evaporated to dryness. The α-sulfoxide ester is generally obtained as an oil which can be obtained crystalline by allowing the oil to stand, or preferably it is obtained crystalline by trituration with diethylether.

The α-sulfoxide formation is illustrated by the following reaction scheme.

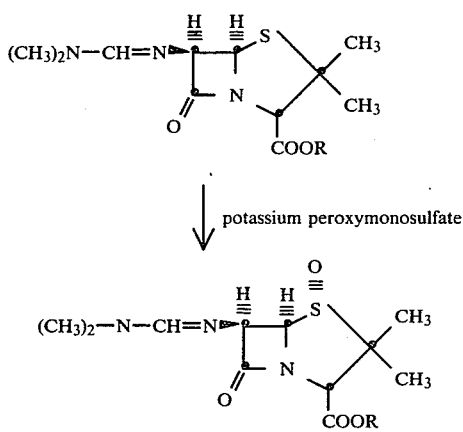

The 7β-dimethylamidino 1α-oxide ester is epimerized as follows to provide the 7α-dimethylamidino 1α-oxide ester of the invention (formula 1). The epimerization is carried out by treating an aqueous solution of the 7β-dimethylamidino 1α-oxide ester with at least one equivalent (mole per mole) of an alkali metal acetate. Preferably, the alkali metal acetate is used in an amount corresponding to about a slight excess up to about a 10% excess. The epimerization is conveniently carried out at about room temperatures, however, epimerization proceeds at a satisfactory rate at a temperature between about 0° C. and about 45° C.

The reaction mixture contains a water miscible organic solvent which is used to solubilize the water insoluble 7β-dimethylamidino 1α-oxide ester. Solvents such as acetonitrile, acetone, and tetrahydrofuran are suitable solvents for this purpose.

Alkali metal acetates which can be used are sodium acetate, potassium acetate, and lithium acetate. Sodium acetate is preferred. The alkali metal acetate can be added in solid form to the aqueous organic solution of 7β-dimethylamidino 1α-oxide ester or alternatively, an aqueous solution of the acetate can be added to a solution of the ester in an organic solvent. The epimerization can likewise be carried out by reverse addition; i.e., by adding a solution of the 7β-epimer in an organic solvent to an aqueous solution of the alkali metal acetate.

The alkali metal epimerization is illustrated by the following reaction scheme.

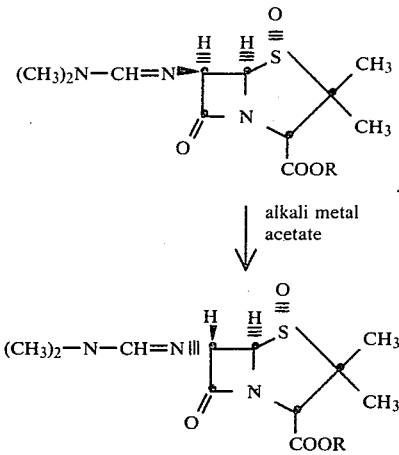

The epimerization proceeds at a rapid rate. For example, on laboratory scale runs carried out at room temperature the epimerization is essentially complete in less than 90 minutes. Commonly, the 7α-epimer is obtained in yields of about 70 percent.

The carboxy-protecting group represented by R in the above formula can be any of the known carboxy-protecting ester groups commonly used in the penicillin art for the temporary protection of the $C_3$ carboxylic acid group. For example, esters such as alkyl and substituted alkyl esters, arylmethyl and substituted arylmethyl esters, and other ester functions are represented by R. Examples of such ester groups are t-butyl, 2,2,2-trichloroethyl, 2,2,2-tribromoethyl, 2-iodoethyl, methoxymethyl, benzyl, p-nitrobenzyl, p-methoxybenzyl, diphenylmethyl, 4,4'-dimethoxydiphenylmethyl, phenacyl, and p-chlorophenacyl. The ester group R functions to protect or block the acidic carboxylic acid group from untoward reactions, or from participation in subsequent reactions used to convert these intermediates to the 1-oxa-β-lactam antibiotics as described hereinafter.

The amidine compounds of the invention are basic compounds which form acid addition salts with strong acids. For example, salts are formed with the mineral acids, hydrochloric acid, hydrobromic acid, and sulfuric acid; and with the sulfonic acids, such as benzenesulfonic acid, toluenesulfonic acid, p-chlorobenzenesulfonic acid, and p-bromobenzenesulfonic acid.

The acid addition salts formed with the free base amidino penicillin ester and strong acids are stable forms of the dimethylamidino sulfoxide esters which can be used for maintaining supplies of the compounds in stable form for later use. The free base amidino penicillin ester form is readily obtained from the salt form on treatment with a suitable base followed by extraction of the free base form with a water immiscible organic solvent.

The compounds of the invention are useful intermediates in the synthesis of 7β-acylamino-7α-methoxy-1-oxa-β-lactam antibiotics as described by T. Tsuji, et al., U.S. Pat. No. 4,220,766. As is described in this patent, a 6α-acylaminopenicillanic acid ester sulfoxide is converted to an epioxazoline represented by the formula

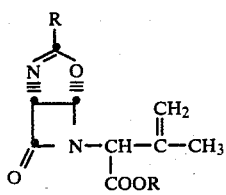

wherein R is the residue of the 6α-acylamino group of the penicillin sulfoxide. The 6α-dimethylamidino penicillin α-sulfoxide provided by this invention is converted to a 6α-formamido penicillin sulfoxide ester which is used to prepare the epioxazoline of the above formula wherein R is hydrogen.

The 6α-dimethylamino penicillin is degraded to the 6α-formamido penicillin by treatment with a mild acid, according to the method described by U.S. Pat. No. 4,281,117 issued July 28, 1981.

In the process, the 6α-amidino penicillin ester 1α-oxide is treated with a mild acid such as a carboxylic acid, a percarboxylic acid, or a phenol, which mild acids have a pH of between about 2 and about 5 as measured in water. The mild acid degradation is carried out in an inert organic solvent such as acetone, methylethyl ketone, methyl acetate, ethyl acetate, methylene chloride, acetonitrile, or tetrahydrofuran. The degradation is carried out at a temperature between about 20° C. and about 45° C.

Mild acids which can be used include formic acid, acetic acid, benzoic acid, perbenzoic acid, m-chloroperbenzoic acid, m-chlorobenzoic acid, phenol, the cresols, and the halogenated phenols, e.g., m-chlorophenol, and p-chlorophenol.

The degradation of the 6α-dimethylamidino ester 1α-oxides of the invention is illustrated by the following reaction scheme.

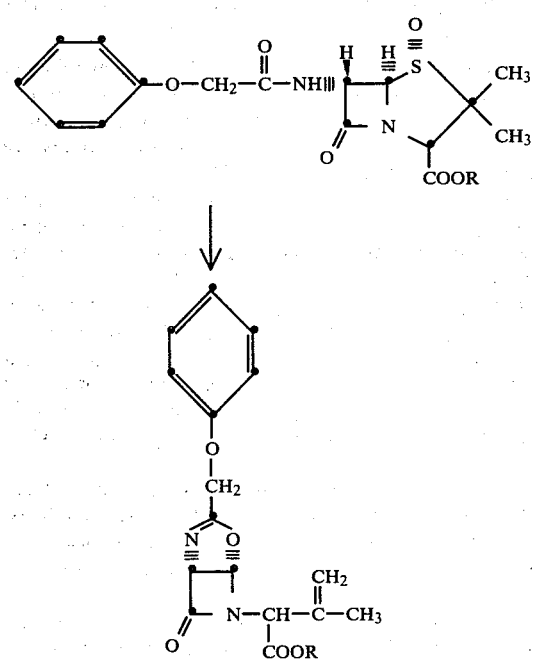

The 6α-formamido penicillin ester sulfoxide is then converted to the epioxazoline as described by U.S. Pat. No. 4,220,766. Alternatively, the 6α-formamido group, obtained via the mild acid degradation, can be hydrolyzed to the 6α-amino penicillin ester 1-oxide, and the latter acylated at the 6α-amino group by conventional acylation procedures with a carboxylic acid to form a 6α-acylamino penicillin ester 1α-oxide. Examples of carboxyic acids which can be used in the acylation are the arylacetic acids such as phenylacetic acid, phenoxyacetic acid, phenylmercaptoacetic acid, benzoic acid, and substituted benzoic acids such as p-chlorobenzoic acid, p-toluic acid, p-cyanobenzoic acid, and like carboxylic acids. A number of such N-acyl-forming carboxylic acids are described in U.S. Pat. No. 4,220,766.

The 6α-formamido group is hydrolyzed by the known procedure in methyl alcohol, dioxane or tetrahydrofuran with a small amount of concentrated hydrochloric acid as described by British Pat. No. 1,290,327. Alternatively, it is N-deformylated with a Lewis acid, eg., phosphorus oxychloride in an inert solvent under anhydrous conditions as described by British Patent Specification No. 1,321,265.

The 6α-acylamino penicillin ester 1α-oxide can then be used to prepare the epioxazoline of the above formula wherein R is the residue of the 6-position acyl group. For example, diphenylmethyl 6α-phenoxyacetylamino-2,2-dimethylpenam-3-carboxylate 1α-oxide is converted to the epioxazoline as shown below.

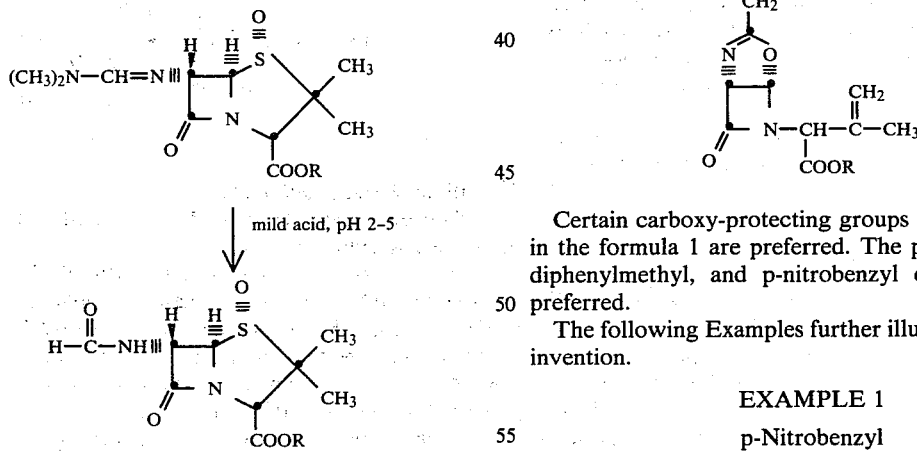

Certain carboxy-protecting groups represented by R in the formula 1 are preferred. The p-methoxybenzyl, diphenylmethyl, and p-nitrobenzyl ester groups are preferred.

The following Examples further illustrate the present invention.

EXAMPLE 1 p-Nitrobenzyl 6β[(dimethylaminomethylene)amino]-2,2-dimethylpenam-3-carboxylate

A solution of 34 mmoles of p-nitrobenzyl 6-amino-2,2-dimethylpenam-3-carboxylate (6APA p-nitrobenzyl ester) in 100 ml of dimethylformamide dimethylacetal was stirred at room temperature for three hours. The reaction mixture was then poured into a stirred mixture of ice water and ethyl acetate and the organic phase separated. The organic phase was layered over water and the pH adjusted to 1.8 with hydrochloric acid. The acidified aqueous layer was separated, slurried with ethyl acetate, and the pH adjusted to 7.5 with 1 N sodium hydroxide. The organic layer was separated, washed with brine, dried over magnesium sulfate, and evaporated to dryness. The product was obtained as a residual oil and was crystallized in trituration with diethyl ether. There were obtained 11 g (80% yield) of the title compound.

NMR spectrum (T60 MHz, DCDl$_3$) showed signal (tau) at 8.58 and 8.32 (2d, 6H, gem CH$_3$), 7.10 (s, 6H, N(CH$_3$)$_2$), 5.59 (s, 1H, C$_3$—H), 4.95 (d, 1H, C$_5$—H), 4.71 (s, 2H, ester CH$_2$), 4.59 (d, 1H, C$_6$—H), 2.51-1.69 (2d, 4H, aromatic H), and 2.42 (s, 1H, NH).

IR spectrum (Nujol mull) showed carbonyl absorption peaks at 1780 and 1730$^{cm-1}$.

Elemental analysis calculated for C$_{18}$H$_{22}$N$_4$O$_5$S: Theory: C, 53.19; H, 5.46; N, 13.78; Found: C, 53.02; H, 5.31; N, 13.57.

EXAMPLE 2 p-Nitrobenzyl 6β-[(dimethylaminomethylene)amino]-2,2-dimethylpenam-3-carboxylate 1α-oxide To a solution of 1.0 g (2.5 mmole) of p-nitrobenzyl 6β-[(dimethylaminomethylene)amino]-2,2-dimethylpenam-3-carboxylate in 27 ml of acetonitrile and 35 ml of water were added 950 mg (3.1 mmole) of potassium peroxymonosulfate (2KHSO$_5$.KHSO$_5$.K$_2$SO$_4$).

The reaction mixture was stirred at room temperature for 45 min. and the pH adjusted to 6.5 with 1 N sodium hydroxide. The mixture was evaporated to remove the acetonitrile and the aqueous concentrate was slurried with ethyl acetate. The pH of the slurry was adjusted to pH 8 and the organic phase was separated, washed with water, dried over magnesium sulfate and evaporated to dryness in vacuo. The product was obtained as a residual oil which was crystallized by titration with diethyl ether. There were obtained 700 mg. (70% yield) of the 1α-oxide product.

NMR (T60 MHz, CDCl$_3$) signals (tau) at 8.87 and 8.35 (2d, 6H, gem di-methyl), 7.14 (s, 6H, N(CH$_3$)$_2$), 5.30 (s, 1H, C$_3$—H), 5.12 (d, 1H, C$_5$—H), 4.76-4.61 (m, 3H, C$_6$—H and ester CH$_2$), 2.52-1.70 (2d, 4H, aromatic H) and 2.32 (s, 1H, NH).

Elemental analysis calculated for C$_{18}$H$_{22}$N$_4$O$_6$S: Theory: C, 51.18; H, 5.25; N, 13.26; Found: C, 51.23; H, 5.44; N, 12.97.

EXAMPLE 3 p-Nitrobenzyl 6α-[(dimethylaminomethylene)amino[-2,2-dimethylpenam-3-carboxylate 1α-oxide To a solution of 844 mg (2 mmole) of p-nitrobenzyl 6β-[(dimethylaminomethylene)amino]-2,2-dimethylpenam-3-carboxylate 1α-oxide in 20 ml of acetonitrile, and in 20 ml of water were added 180 mg (2.2 mmole) of sodium acetate, and the mixture was stirred at room temperature for 1.5 hours. After the reaction, the mixture was evaporated to remove the acetonitrile and the product was extracted from the aqueous concentrate with ethyl acetate. The extract was washed with water, dried over magnesium sulfate and concentrated to a small volume. The product crystallized when the concentrate was diluted with diethyl ether. There were obtained 600 mg (70% yield) of the product.

NMR (T60 MHz, acetone d6/D$_2$O) signals (tau) at 8.74 and 8.38 (2s, 6H, gem dimethyl), 7.10 (s, 6H, N(CH$_3$)$_2$), 5.49 (s, 1H, C$_3$—H), 5.21 (d, 1H, C$_5$—H), 4.96 (d, 1H, C$_6$—H), 4.59 (s, 2H, ester CH$_2$), 2.42 (s, 1H, NH) and 2.35-1.69 (2d, 4H, aromatic H); (T60 MHz, CDCl$_3$) signal (tau at 5.1 (s, 2H, C$_5$ and C$_6$H).

Elemental analysis calculated for C$_{18}$H$_{22}$N$_4$O$_6$S: Theory: C, 51.18; H, 5.25; N, 13.26; Found: C, 51.09; H, 5.07; N, 13.04.

I claim:

1. A process for preparing the 6-epi-amidinopenicillin α-sulfoxide ester of the formula

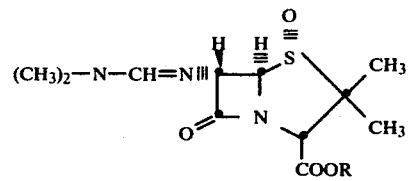

wherein R is a carboxy-protecting group, which comprises mixing in an aqueous medium at a temperature between about 0° C. and about 45° C. a 6β-[(dimethylaminomethylene)amino]-2,2-dimethylpenam-4-carboxylic acid ester 1α-oxide of the formula

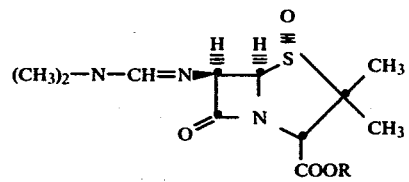

with an alkali metal acetate.

2. The process of claim 1 wherein the alkali metal acetate is sodium acetate.

3. The process of claim 1 wherein the alkali metal acetate is mixed in a ratio of at least one mole per mole of the 6β-[(dimethylaminomethylene)amino]-2,2-dimethylpenam-4-carboxylic acid ester 1α-oxide.

4. The process of claim 3 wherein R is p-nitrobenzyl, p-methoxybenzyl, or diphenylmethyl.

5. The process of claim 3 wherein R is p-nitrobenzyl.

* * * * *